United States Patent
Kahn et al.

(10) Patent No.: US 8,362,292 B2
(45) Date of Patent: Jan. 29, 2013

(54) PROCESS FOR PRODUCING ALLYL ACETATE

(75) Inventors: Andrew P. Kahn, Eagleville, PA (US); Elizabeth I. Ross-Medgaarden, Humble, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 13/571,885

(22) Filed: Aug. 10, 2012

(65) Prior Publication Data

US 2012/0310006 A1  Dec. 6, 2012

Related U.S. Application Data

(63) Continuation of application No. 12/586,966, filed on Sep. 30, 2009, now Pat. No. 8,263,801.

(51) Int. Cl.
*C07C 67/05* (2006.01)
*C07C 69/02* (2006.01)
(52) U.S. Cl. .................................. 560/243; 560/231
(58) Field of Classification Search ................. None
See application file for complete search history.

(56) References Cited

U.S. PATENT DOCUMENTS 4,010,198 A * 3/1977 Roscher et al. ............... 560/245

\* cited by examiner

*Primary Examiner* — Karl J Puttlitz

(57) ABSTRACT

A process for producing allyl acetate is disclosed. The process comprises reacting a feed comprising propylene, acetic acid, oxygen, and carbon dioxide in the presence of a supported palladium catalyst. The feed comprises from 2 to 6 mole percent carbon dioxide, which improves the selectivity to allyl acetate.

24 Claims, No Drawings

PROCESS FOR PRODUCING ALLYL ACETATE

This application is a continuation of application Ser. No. 12/586,966, filed Sep. 30, 2009.

FIELD OF THE INVENTION

This invention relates to a process for producing allyl acetate from propylene, acetic acid, and oxygen in the presence of a supported palladium catalyst and carbon dioxide.

BACKGROUND OF THE INVENTION

Oxidation of propylene in the presence of acetic acid catalyzed by a palladium catalyst to produce allyl acetate is known. The process includes a reaction (acetoxylation) of propylene with oxygen and acetic acid to form a mixture comprising allyl acetate, propylene, oxygen, acetic acid, water, carbon dioxide, and possibly other inert gases. The reaction mixture is typically separated into a gas stream comprising propylene, oxygen, acetic acid, water, and carbon dioxide, and a liquid stream comprising allyl acetate, acetic acid, and water. Allyl acetate can be separated from the liquid stream. At least a portion of the acetic acid and water separated from the liquid stream is recycled to the acetoxylation reaction.

The gas stream is also generally recycled to the acetoxylation reaction (U.S. Pat. Nos. 3,970,713 and 4,010,198). U.S. Pat. No. 4,010,198 discloses that the feed entering the reactor contains significant concentration of carbon dioxide. In Example 1 of U.S. Pat. No. 4,010,198, the feed contains 10 volume percent carbon dioxide. In Example 4, it contains 65 volume percent carbon dioxide. A higher carbon dioxide concentration in the feed to the acetoxylation reaction decreases the productivity of the process. In addition, the recycle gas needs to be pressurized before it can enter the reactor because the acetoxylation is performed at a higher pressure. Consequently, a higher carbon dioxide concentration in the recycle gas requires higher energy consumption for compressing the recycle gas.

SUMMARY OF THE INVENTION

This invention is a process for producing allyl acetate. The process comprises reacting a feed comprising propylene, acetic acid, oxygen, and carbon dioxide in the presence of a supported palladium catalyst. The feed comprises from 2 to 6 mole percent (mol %) carbon dioxide.

DETAILED DESCRIPTION OF THE INVENTION

The process comprises reacting a feed comprising propylene, acetic acid, oxygen, and carbon dioxide in the presence of a supported palladium catalyst, wherein the feed comprises from 2 to 6 mol % carbon dioxide.

The process uses a supported palladium catalyst. The amount of palladium is 0.1 to 5.0 weight percent (wt %), preferably 0.3 to 1.5 wt % of the supported catalyst.

In addition to palladium, the catalyst may comprise a Group 11 element, i.e., gold, copper, silver, and mixtures thereof. The content of gold, copper, or silver may be in the range of 0 to 5.0 wt %, preferably in the range of 0.02 to 1.0 wt % of the supported catalyst.

The catalyst may additionally comprise an activator. An activator is an alkali or alkaline earth metal compound, examples of which are hydroxides, acetates, nitrates, carbonates, and bicarbonates of potassium, sodium, cesium, magnesium, barium, and the like. Potassium and cesium salts are preferred activators. The activator content may be in the range of 0 to 15 wt %, preferably 1.5 to 10 wt % of the supported catalyst.

The supported palladium catalyst comprises a carrier. Suitable carriers include alumina, silica, titania, carbon, and like, and mixtures thereof. Preferably, the carrier has a surface area of at least 1 $m^2/g$ and a pore volume of 0.1 to 1.5 mL/g.

The catalyst may be prepared by many techniques. Examples of these techniques are disclosed in U.S. Pat. Nos. 3,925,452, 5,011,980, 6,303,536, and U.S. Pat. Appl. Pub. Nos. 2006/0167307 and 2006/0247462.

In preparing the catalyst, the carrier can be simultaneously or successively impregnated with a palladium compound, optionally a Group 11 metal salt, and optionally an activator. Preferably, the impregnation is performed in aqueous solutions.

Suitable palladium compounds include palladium chloride, sodium chloropalladate, palladium nitrate, palladium sulfate, the like, and mixtures thereof. Suitable Group 11 metal salts include chlorides, nitrates, sulfates. Examples are tetrachloroauric acid, sodium tetrachloroaurate, copper chloride, copper nitrate, copper sulfate, silver nitrate, the like, and mixtures thereof. Suitable activators include hydroxides, carbonates, bicarbonates, metasilicates of alkali and alkaline earth metals, the like, and mixtures thereof.

One method to impregnate the carrier involves contacting the carrier with an aqueous solution containing both a palladium compound and a Group 11 metal salt. In another method, the carrier is contacted with a palladium compound and a Group 11 metal salt in separate steps.

An alkali metal, alkaline earth metal, or ammonium compound is optionally contacted with the carrier during or after the carrier is impregnated with the palladium compound and optionally the Group 11 metal salt. These compounds help the palladium compound and the Group 11 metal salts, if used, to bind to the carrier. Suitable alkali metal, alkaline earth metal, or ammonium compounds include their hydroxides, carbonates, bicarbonates, metasilicates, and the like, and mixtures thereof. The impregnated carrier is optionally washed with water or an aqueous solution.

The impregnated carrier is usually calcined (heated at an elevated temperature) in a non-reducing atmosphere. Preferably, the calcination of the impregnated carrier is carried out at a temperature in the range of about 100 to about 600° C., more preferably, in the range of 250 to 500° C. Suitable non-reducing gases for the calcination include helium, nitrogen, argon, oxygen, air, carbon dioxide, the like, and mixtures thereof. Preferably, the calcination is carried out in an atmosphere of nitrogen, oxygen, air, or mixtures thereof.

Following the calcination, the resulting material is normally reduced to convert at least a portion of the palladium and the Group 11 metal, if used, to the corresponding elements with zero valence. The reduction is performed by contacting it with a reducing agent. Suitable reducing agents include hydrogen, carbon monoxide, olefins, aldehydes, alcohols, hydrazine, the like, and mixtures thereof. Temperatures employed for the reduction are in the range of 20 to 700° C.

Hydrogen gas is a preferred reducing agent. Generally, a mixed gas containing hydrogen and another gas such as argon, helium, nitrogen, or the like, is used. Preferably, the reduction temperature is in the range of 300 to 700° C. Most preferably, the reduction temperature is in the range of 450 to 550° C.

The feed to the reaction comprises propylene, acetic acid, oxygen, and carbon dioxide. The feed preferably comprise an inert gas. Examples of suitable inert gases include propane, nitrogen, helium, argon, the like, and mixtures thereof. The amount of inert gas in the feed is preferably in the range of 10 to 55 mol %, more preferably from 15 to 25 mol %.

The reaction mixture comprises allyl acetate, propylene, oxygen, acetic acid, water, and carbon dioxide. Typically, the reaction mixture is partially condensed to form a liquid stream which can be separated from a remaining gas stream. The liquid stream typically contains 5 to 20 wt % allyl acetate, 20 to 40 wt % acetic acid, and about 40 to 60 wt % water. Depending upon the concentrations of components, the liquid stream may be separated into an organic stream comprising allyl acetate, and an aqueous stream comprising water and acetic acid. Preferably, the aqueous stream or a portion of it (called "recycle liquid") is recycled to the reaction.

The gas stream can be compressed and recycled. There are various techniques to recycle the gas stream. In one example, a recycle gas is passed through an evaporator containing acetic acid and water so that the recycle gas is charged with the requisite quantity of acetic acid and water from the evaporator before it enters the reactor.

Depending upon the temperature and pressure at which the gas stream is separated from the liquid stream, the gas stream may contain certain quantities of condensable products such as water, allyl acetate, and acetic acid. Such a gas stream can be directly recycled to the acetoxylation reaction.

The feed to the acetoxylation reaction usually includes not only the components introduced to the process including propylene, oxygen, and acetic acid, but also any recycle stream (i.e., the recycle gas and the recycle liquid) from the process. The content of propylene in the feed is generally between 20 to 80 mol %, preferably 40 to 70 mol %. A propylene content of greater than 50 mol % is particularly desirable. Commercially available products such as polymer grade propylene and chemical grade propylene are suitable sources of propylene. Preferably, the source of propylene has a purity of at least 90 mol %.

The feed comprises typically 8 to 20 mol %, preferably from 10 to 18 mol %, acetic acid.

The feed comprises typically 2 to 8 mol %, preferably 3 to 6 mol % oxygen. The oxygen source in the present invention is not limited, and may be supplied in the form of a mixture with a gas such as nitrogen or carbon dioxide. Air may be used. Preferably the oxygen source has a purity of at least 90 mol %, more preferably at least 95 mol %. The allowed oxygen concentration in the feed is determined by the flammability limit. The flammability limit depends on temperature, pressure, and composition. It can be shifted by additional components, such as acetic acid, water, nitrogen, carbon dioxide, and argon.

The feed comprises from 2 to 6 mol %, more preferably from 3 to 6 mol %, most preferably from 4 to 6 mol % carbon dioxide. Carbon dioxide not only serves as a diluent in the feed, but also improves the selectivity to allyl acetate and suppresses the formation of carbon dioxide (see Tables 1 and 2).

The concentration of carbon dioxide in the feed may be controlled by several techniques. For example, carbon dioxide can be removed from the recycle gas by adsorption, scrubbing, or a purge so that the carbon dioxide concentration in the feed remains more or less constant.

The feed may comprise water. The amount of water present in the feed is preferably from 0 to 5 mol %, more preferably from 1 to 4 mol %.

The feed is a gas under the reaction conditions. Accordingly, the quantities of acetic acid and water in the feed are adjusted so that the feed is gaseous under the temperature and pressure selected for the reaction. The reaction is generally performed at a temperature in the range of 100 to 250° C., preferably 120 to 200° C. Generally, the reaction pressure is in the range of 15 to 450 psig, preferably in the range of 30 to 150 psig.

The reaction may be performed in a fixed bed reactor or a fluidized bed reactor, or the like. A fixed bed reactor is preferred. In one example, a multitubular fixed bed reactor is used. Typically the tube diameter is from 1" to 4" (U.S. Pat. No. 3,970,713).

The feed preferably passes through the catalyst at a space velocity of in the range of 10 to 15,000 $h^{-1}$, more preferably in the range of 300 to 8,000 $h^{-1}$.

Propylene conversion is generally 3 to 15%, and that of acetic acid 9 to 45%. Oxygen conversion can be up to 90%.

EXAMPLE 1

Catalyst A

A catalyst precursor, Pd/Au/alumina, is prepared by following the procedure disclosed in Example 1 of U.S. Pat. No. 6,022,823. After the material (43 g) is reduced, it is mixed with an aqueous cesium acetate solution (25 wt %, 16.5 g). The sample is then dried overnight at 120° C. in air. The calculated composition of the obtained catalyst (Catalyst A) is: 1.1 wt % Pd, 0.5 wt % Au, and 6.0 wt % Cs.

EXAMPLE 2

Catalyst B $NaAuCl_4.2H_2O$ (0.57 g), $Na_4PdCl_4.3H_2O$ (1.71 g), and water (16 g) are added to a 150-mL beaker equipped with a stirrer bar. $NaHCO_3$ (1.68 g) is added in the beaker in three equal portions. Carbon dioxide is slowly released. The solution formed is added dropwise to titania extrudates (27 $m^2$/g, crushed to 14×30 mesh) while they are tumbling in a rotating bowl.

While the impregnated solid is rotating in the bowl, it is heated with a hot air gun until it is free flowing. The dried solid is further dried in an oven at 80° C. for 12 h.

The above solid (50 g) is rinsed with hot (80° C.) deionized water (4 L) to remove chloride from the solid. The washed solid is dried at 80° C. for 6 h, further dried at 125° C. for 2 h, then cooled to room temperature. It is then heated under an air flow at a rate of 50 standard liters per hour from room temperature to 120° C. at a rate of 20° C./min, held at 120° C. for 10 min, heated from 120 to 220° C. at a rate of 1.5° C./min, held at 220° C. for 3.5 h, then cooled to room temperature at 40° C./min. The solid is then purged with nitrogen (50 standard liters per hour) for 30 min.

The above material is treated with a gas mixture containing hydrogen and helium in a molar ratio of 5:95 (50 standard liters per hour). The temperature is raised from room temperature to 220° C. at a rate of 30° C./min, held at 220° C. for 10 min, raised again to 500° C. at a rate of 5° C./min, and held at 500° C. for 3.25 h. It is then cooled to room temperature while being purged with nitrogen (50 standard liters per hour) for 15 min. A catalyst precursor is obtained.

An aqueous cesium acetate solution is prepared by dissolving cesium acetate (50 g) in water (150 g). Copper acetate monohydrate (0.19 g) is added to a portion of the above aqueous cesium acetate solution (6.1 g). The obtained solution is added dropwise to a portion of the above catalyst precursor (19.6 g). The resulted material is dried overnight at 120° C. in air. The calculated composition of the obtained catalyst (Catalyst B) is: 0.9 wt % Pd, 0.5 wt % Au, 0.3 wt % Cu, and 4.9 wt % Cs.

EXAMPLE 3

Catalyst C

Catalyst C is prepared according to the procedure of Example 2 except that a solution is prepared by mixing copper acetate monohydrate (0.41 g) and the CsOAc solution (6.1 g). The obtained solution is added dropwise to a portion of the catalyst precursor prepared in Example 2 (19.6 g). The product is dried overnight at 120° C. in air. The calculated composition of the obtained catalyst (Catalyst C) is: 1.1 wt % Pd, 0.5 wt % Au, 0.3 wt % Cu, and 6.0 wt % Cs.

EXAMPLE 4

Catalyst D

Catalyst D is prepared according to the procedure of Example 2 except that a solution is prepared by mixing copper acetate monohydrate (0.06 g) and a potassium acetate solution (12.8 wt %, 7.7 g). The solution is added to a portion of the catalyst precursor prepared in Example 2 (20 g), which is then dried overnight at 120° C. The calculated composition of Catalyst D is: 1.1 wt % Pd, 0.5 wt % Au, 0.1 wt % Cu, and 1.9 wt % K.

EXAMPLE 5

Catalyst E

Catalyst E is prepared according to the procedure of Example 2 except that a solution is prepared by mixing copper acetate monohydrate (0.19 g) and a potassium acetate solution (12.8 wt %, 7.4 g). The solution is added to a portion of the catalyst precursor prepared in Example 2 (20 g), which is then dried overnight at 120° C. The calculated composition of Catalyst E is: 1.0 wt % Pd, 0.5 wt % Au, 0.3 wt % Cu, and 1.8 wt % K.

EXAMPLE 6

Catalyst F

A solution is prepared by dissolving $Na_2PdCl_4 \cdot 3H_2O$ (1.4 g), $NaHCO_3$ (1.4 g) in water (10 g). The solution is used to impregnate alpha alumina (5/16" pellets, surface area=4 m²/g, 35 g) according to procedure of Example 2. A catalyst precursor (Precursor G) is produced.

A second solution is prepared by mixing copper acetate monohydrate (0.19 g) and a potassium acetate solution (12.8 wt %, 7.5 g). The solution is added to 20 g of Precursor G prepared above, which is then dried overnight at 120° C. The calculated composition of catalyst obtained (Catalyst F) is: 1.2 wt % Pd, 0.3 wt % Cu, and 1.7 wt % K.

EXAMPLE 7

Acetoxylation with Catalyst A

A stainless steel reactor (0.97" ID equipped with a 0.25" thermowell at the center) is packed with a mixture of Catalyst A (10 mL) and glass beads (1 mm diameter, 30 mL). The reactor is heated by a sand bath to 140° C. A feed containing 58 mol % propylene, 3 mol % oxygen, 15 mol % acetic acid, carbon dioxide (concentrations shown in Table 1), and nitrogen (balance) is fed to the reactor at a flow rate of 22 standard liters per hour. The reactor pressure is controlled at 80 psig. The reaction mixture is cooled to room temperature and separated by a vapor/liquid separator to a liquid stream and a vapor stream. The reaction continues for 500 h. The liquid stream and the vapor stream are analyzed by gas chromatography (GC). The results are listed in Table 1.

Table 1 shows that 2 mol % carbon dioxide in the feed improves the selectivity to allyl acetate and reduces the selectivity to carbon dioxide. At about 4 mol % carbon dioxide, the selectivity to carbon dioxide is reduced to an undetectable level.

EXAMPLES 8-12

Acetoxylation with Catalysts B, C, D, E, and F

The procedure of Example 7 is repeated except that Catalysts B, C, D, E, and F are used instead of Catalyst A. The results are listed in Table 2. Table 2 shows that selectivities to allyl acetate are improved for various supported palladium catalysts by including 4.0 mol % carbon dioxide in the feed.

TABLE 1

| Test | Feed Carbon Dioxide (mol %) | Selectivity to Carbon Dioxide (%) | Selectivity to AAc* (%) | Selectivity to ADAc* (%) | STY* (g AAc/ L cat/h) |
| --- | --- | --- | --- | --- | --- |
| Comparative 7.1 | 0 | 3.6 | 91.0 | 1.3 | 263 |
| Comparative 7.2 | 1.0 | 4.0 | 90.7 | 1.1 | 254 |
| 7.3 | 2.0 | 2.6 | 92.3 | 1.1 | 263 |
| 7.4 | 3.0 | 1.2 | 92.9 | 1.0 | 251 |
| 7.5 | 4.0 | 0 | 94.4 | 1.1 | 251 |
| 7.6 | 5.0 | 0 | 94.2 | 1.1 | 245 |
| 7.7 | 5.7 | 0 | 94.3 | 1.1 | 242 |

*AAc = allyl acetate; ADAc = allyl diacetate; STY = space time yield, expressed as grams of allyl acetate produced per liter of catalyst per hour.

TABLE 2

| Test | Catalyst | Feed Carbon Dioxide (mol %) | Selectivity to Carbon Dioxide (%) | Selectivity to AAc* (%) | Selectivity to ADAc* (%) | STY* (g AAc/L cat/h) |
| --- | --- | --- | --- | --- | --- | --- |
| Comparative 8.1 | B | 0 | 1.2 | 94.0 | 1.7 | 330 |
| 8.2 | B | 4.0 | 0 | 95.2 | 1.6 | 318 |
| Comparative 9.1 | C | 0 | 1.5 | 97.8 | 0.2 | 210 |
| 9.2 | C | 4.0 | 0 | 98.2 | 0.2 | 200 |
| Comparative 10.1 | D | 0 | 0.7 | 97.8 | 0.2 | 206 |
| 10.2 | D | 4.0 | 0 | 98.4 | 0.2 | 203 |
| Comparative 11.1 | E | 0 | 1.1 | 94.2 | 1.4 | 324 |
| 11.2 | E | 4.0 | 0 | 95.4 | 1.3 | 321 |

TABLE 2-continued

| Test | Catalyst | Feed Carbon Dioxide (mol %) | Selectivity to Carbon Dioxide (%) | Selectivity to AAc* (%) | Selectivity to ADAc* (%) | STY* (g AAc/L cat/h) |
|---|---|---|---|---|---|---|
| Comparative 12.1 | F | 0 | 0.6 | 96.8 | 0.6 | 278 |
| 12.2 | F | 4.0 | 0 | 97.5 | 0.6 | 263 |

*AAc = allyl acetate; ADAc = allyl diacetate; STY = space time yield, expressed as grams of allyl acetate produced per liter of catalyst per hour.

We claim:

1. A process for producing allyl acetate, comprising reacting a feed comprising propylene, acetic acid, oxygen, and carbon dioxide in the presence of a supported palladium catalyst, wherein the feed comprises from 2 to 6 mol % carbon dioxide to form a reaction mixture comprising allyl acetate, propylene, oxygen, acetic acid, water, and carbon dioxide, further wherein the concentration of the carbon dioxide in the feed is controlled at a constant concentration; the reaction mixture is partially condensed to form a liquid stream and a gas stream; the liquid stream is further separated into an organic stream and an aqueous stream; and at least a portion of the aqueous stream and at least a portion of the gas stream are recycled to the feed.

2. The process of claim 1 wherein the supported palladium catalyst comprises from 0.1 to 5.0 wt % palladium.

3. The process of claim 1 wherein the feed comprises from 4 to 6 mol % carbon dioxide.

4. The process of claim 1 wherein the feed comprises 1 to 4 mol % water.

5. The process of claim 1 wherein the feed comprises greater than 50 mol % propylene.

6. The process of claim 1 wherein the feed comprises an inert gas selected from the group consisting of propane, argon, nitrogen, and mixtures thereof.

7. The process of claim 6 wherein the feed comprises 10 to 55 mol % inert gas.

8. The process of claim 1 wherein the feed comprises 8 to 20 mol % acetic acid.

9. The process of claim 1 wherein the feed comprises from 2 to 8 mol % of oxygen.

10. The process of claim 1 wherein the liquid stream comprises 5 to 20 wt % allyl acetate, 20 to 40 wt % acetic acid, and 40 to 60 wt % water.

11. The process of claim 1 wherein the organic stream comprises allyl acetate and the aqueous stream comprises water and acetic acid.

12. The process of claim 1 wherein all of the aqueous stream is recycled to the feed.

13. The process of claim 1 wherein propylene has a purity of at least 90 mol %.

14. The process of claim 1 wherein the selectivity to allyl acetate is improved when compared to a process wherein less than 2 mol % carbon dioxide is presented in the feed.

15. The process of claim 1 wherein the formation of carbon dioxide is suppressed when compared to a process wherein less than 2 mol % carbon dioxide is present in the feed.

16. The process of claim 1 wherein the supported palladium catalyst further comprises gold, copper, silver, or mixtures thereof.

17. The process of claim 16 wherein the supported palladium catalyst comprises from 0.02 to 5.0 wt % of a Group 11 element or mixtures of Group 11 elements.

18. The process of claim 1 wherein the supported palladium catalyst further comprises an activator.

19. The process of claim 18 wherein the activator comprises a Group 1 salt or combinations thereof.

20. The process of claim 19 wherein the activator is present in an amount from 1.5 to 15 wt % based on the supported palladium catalyst.

21. The process of claim 1 wherein the palladium catalyst further comprises a carrier.

22. The process of claim 21 wherein the carrier is alumina, silica, titania, carbon, or a mixture thereof.

23. The process of claim 21 wherein the carrier has a surface area of at least 1 $m^2/g$.

24. The process of claim 21 wherein the carrier has a pore volume of 0.1 to 1.5 mL/g.

* * * * *